United States Patent
Ohdaira

(10) Patent No.: US 12,329,152 B2
(45) Date of Patent: Jun. 17, 2025

(54) CHARGED NANOBUBBLE DISPERSION LIQUID, METHOD OF MANUFACTURING THE SAME, MANUFACTURING APPARATUS FOR THE SAME, AND A METHOD FOR CONTROLLING GROWTH RATE OF MICROORGANISMS AND PLANTS USING THE LIQUID

(71) Applicant: Takeshi Ohdaira, Saitama (JP)

(72) Inventor: Takeshi Ohdaira, Saitama (JP)

( * ) Notice: Subject to any disclaimer, the term of this patent is extended or adjusted under 35 U.S.C. 154(b) by 1316 days.

(21) Appl. No.: 16/770,522

(22) PCT Filed: Dec. 7, 2018

(86) PCT No.: PCT/JP2018/045186
§ 371 (c)(1),
(2) Date: Apr. 22, 2021

(87) PCT Pub. No.: WO2019/112062
PCT Pub. Date: Jun. 13, 2019

(65) Prior Publication Data
US 2021/0244021 A1 Aug. 12, 2021

(30) Foreign Application Priority Data
Dec. 8, 2017 (JP) ................................ 2017-236437

(51) Int. Cl.
| | | |
|---|---|---|
| *A01N 25/04* | (2006.01) | |
| *A01N 25/34* | (2006.01) | |
| *A01N 59/00* | (2006.01) | |
| *A01N 59/04* | (2006.01) | |
| *A01P 21/00* | (2006.01) | |
| *B01F 23/23* | (2022.01) | |
| *B01F 23/233* | (2022.01) | |
| *B01F 23/2375* | (2022.01) | |
| *C12N 1/12* | (2006.01) | |
| *B01F 101/00* | (2022.01) | |

(52) U.S. Cl.
CPC ............ *A01N 25/04* (2013.01); *A01N 25/34* (2013.01); *A01P 21/00* (2021.08); *B01F 23/233* (2022.01); *B01F 23/2375* (2022.01); *B01F 23/238* (2022.01); *C12N 1/12* (2013.01); *B01F 2101/2204* (2022.01)

(58) Field of Classification Search
None
See application file for complete search history.

(56) References Cited

U.S. PATENT DOCUMENTS

| | | | | |
|---|---|---|---|---|
| 9,382,136 | B2 * | 7/2016 | Han | ................... B01F 31/85 |
| 9,512,398 | B2 * | 12/2016 | Wood | ................ B01F 23/233 |
| 2007/0071685 | A1 | 3/2007 | Schneider et al. | |
| 2007/0189972 | A1 | 8/2007 | Chiba et al. | |
| 2015/0250728 | A1 | 9/2015 | Murata et al. | |

FOREIGN PATENT DOCUMENTS

| | | |
|---|---|---|
| JP | 2007-515470 A | 6/2007 |
| JP | 2009-131769 A | 6/2009 |
| JP | 2009-131770 A | 6/2009 |
| JP | 2009-246042 A | 10/2009 |
| JP | 2010-162517 A | 7/2010 |
| JP | 2012-108073 A | 6/2012 |
| JP | 2015-097509 A | 5/2015 |
| JP | 2016-053004 A | 4/2016 |
| JP | 2016-142599 A | 8/2016 |
| JP | WO2014050910 A | 8/2016 |
| WO | WO-2018030621 A1 * | 2/2018 ............ B63B 25/02 |

OTHER PUBLICATIONS

Nirmalkar, N. et al., "On the existence and stability of bulk nanobubbles," Langmuir, vol. 34, p p. 10964-10973 (2018).*
Machine translation of JP 2006-042785 (Feb. 16, 2006).*
International Search Report and Written Opinion for PCT/JP2018/045186 mailed Mar. 26, 2019.

* cited by examiner

*Primary Examiner* — John Pak
(74) *Attorney, Agent, or Firm* — Greer, Burns & Crain, Ltd

(57) ABSTRACT

The present invention provides positively or negatively charged nanobubbles, with the goal to clarify the effects of positively or negatively charged nanobubbles on microorganism and plant growth. The present invention also provides charged nanobubble dispersion liquid that contains $10^5$ to $10^{10}$ fine bubbles. The fine bubbles are dispersed in the liquid, are positively or negatively charged, have an average particle size of 10 nm to 500 nm, and have a zeta potential of 10 mV to 200 mV.

1 Claim, 7 Drawing Sheets

Fig. 1. Frequency distribution of Density by charge of positively charged nanobubbles measured by ZetaView

Result
Mobility: 2.24 ± 0.04 µm/sec/V/cm, @ 25°C: 2.20 µm/sec/V/cm
ZP Factor 12.6 (Smoluchowski):
Zeta Potential @ 25 °C: 28.20 ± 0.45 mV
Zeta Potential Distribution: 28.20 mV FWHM 29.65 (SL1/2)
Concentration  83.22E+6 Particles / mL

Quality
Number of Traced Particles: 2297
ΔSL: 5.39 mV
Profile Quality: 7 / 11

Analysis Parameters
Max Size: 1000, Min Size: 5, Min Brightness: 20

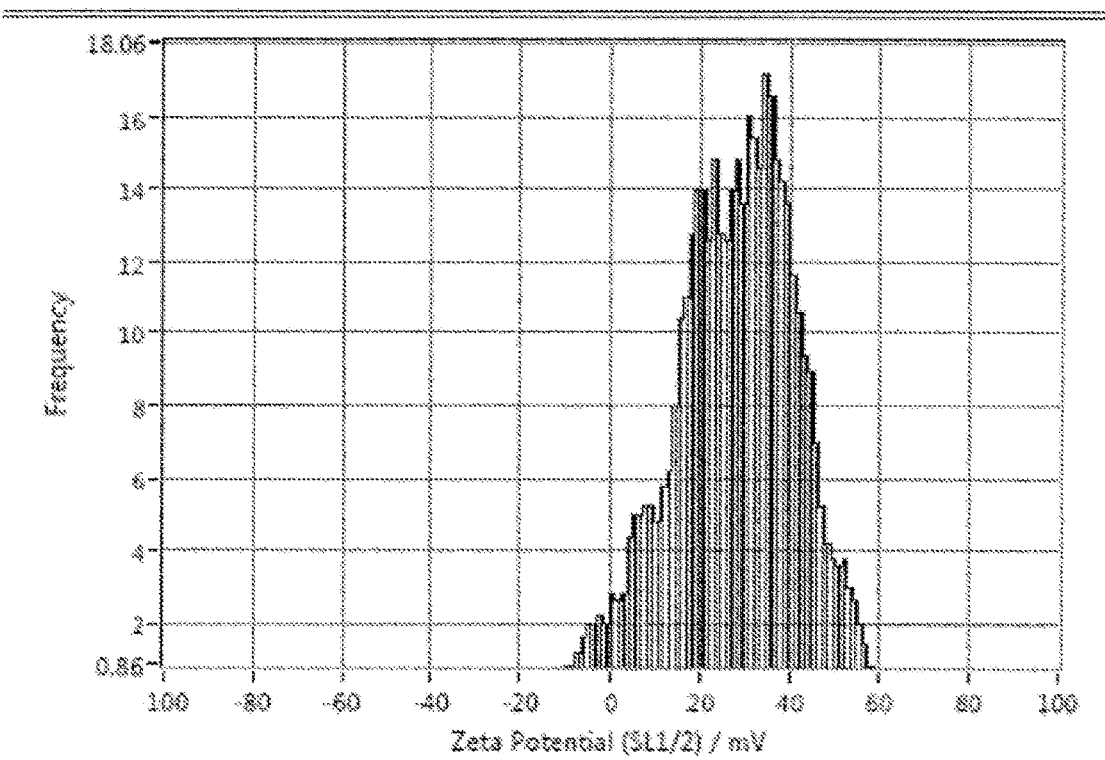

Fig. 2. Frequency distribution of Density by charge of negatively charged nanobubbles measured by ZetaView

Result
Mobility: -7.24 ± 0.20 µm/sec/V/cm, @ 25°C: -7.15 µm/sec/V/cm
ZP Factor 12.7 (Smoluchowski):
Zeta Potential @ 25 °C: -91.62 ± 2.57 mV
Zeta Potential Distribution: -91.62 mV FWHM 29.41 (SL1/2)
Concentration 216.44E+6 Particles / mL

Quality
Number of Traced Particles: 4369
ΔSL: 31.82 mV
Profile Quality: 11 / 11

Analysis Parameters
Max Size: 1000, Min Size: 5, Min Brightness: 20

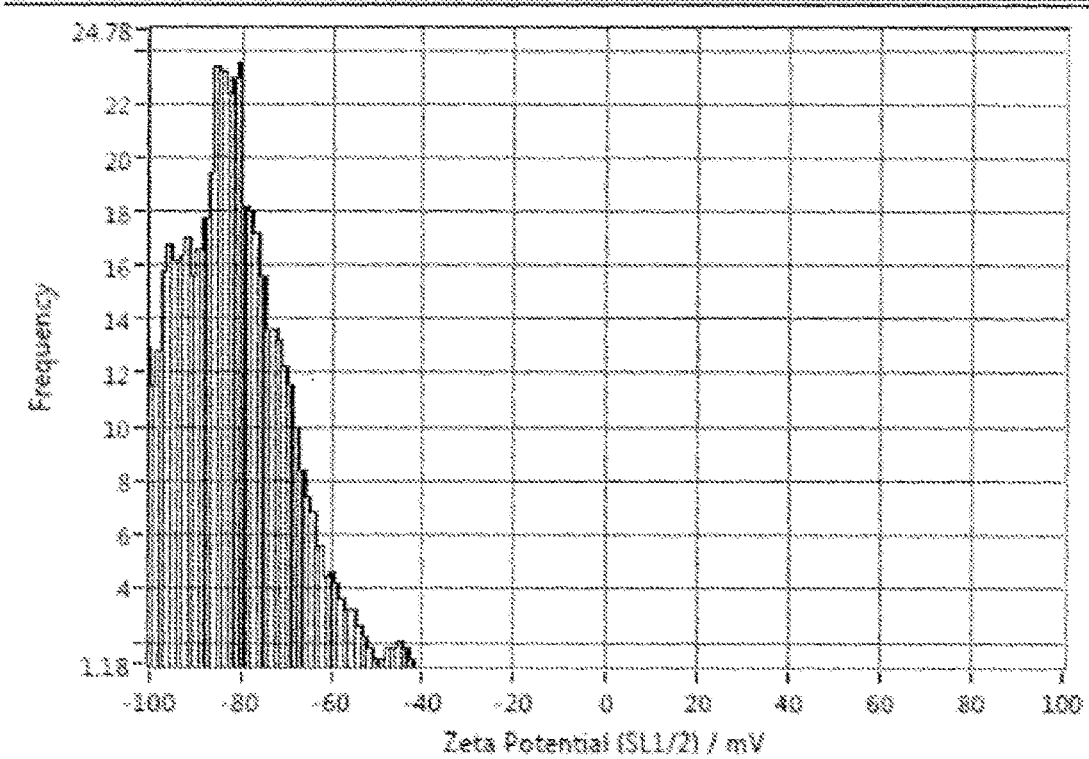

Fig. 3. Chlorophyll production by photosynthesis of Chlamydomonas of each positive, negative and control group using nanobubbles in which air is enclosed
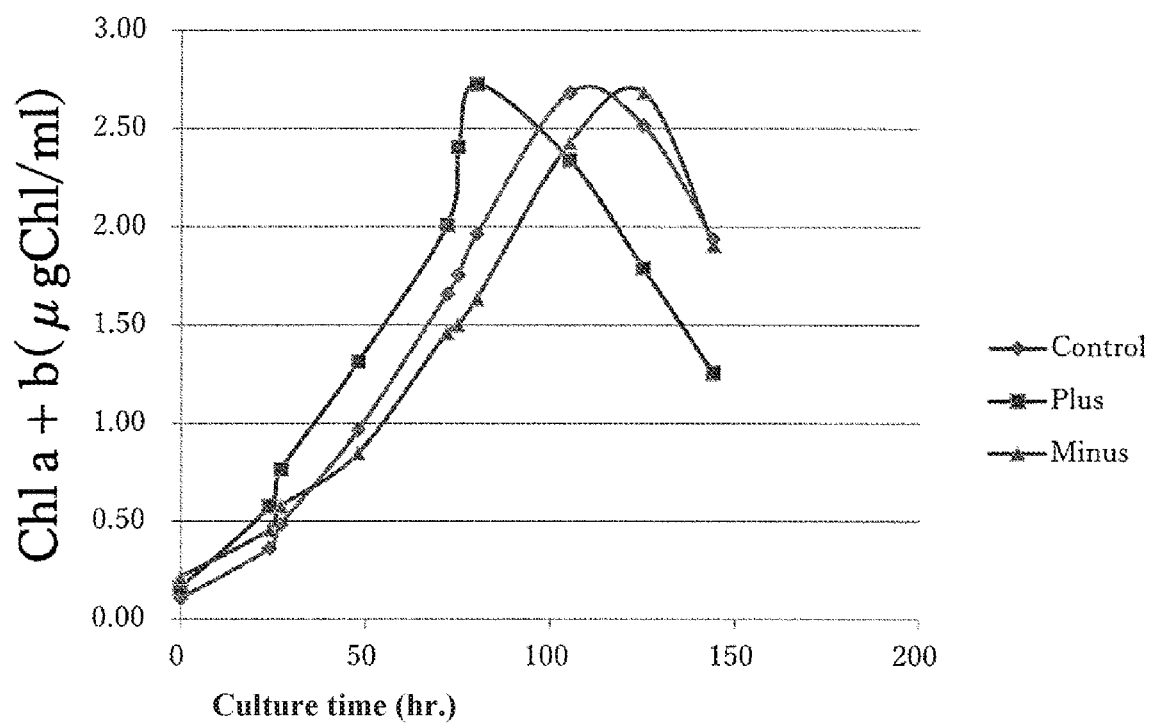

Fig. 4. Chlorophyll production by photosynthesis of Chlamydomonas of each positive, negative and control group using nanobubbles in which carbon dioxide gas is enclosed
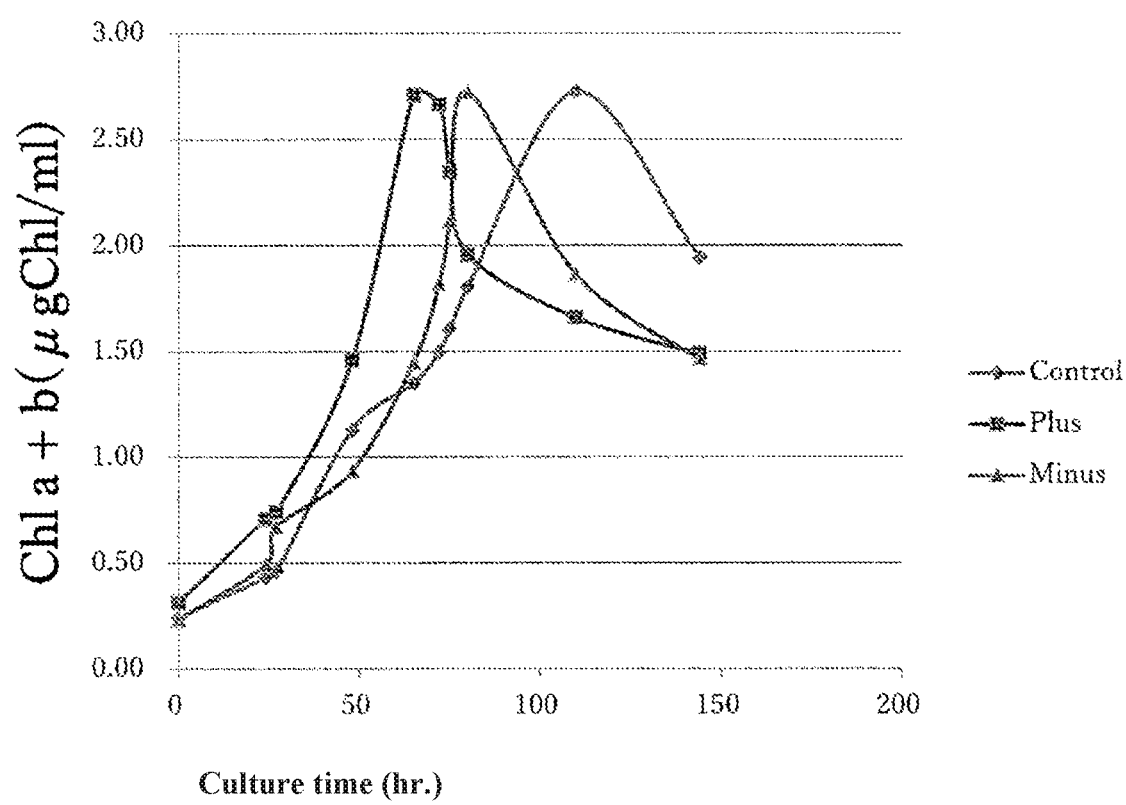

Fig. 5. Chlorophyll production by photosynthesis of chlamydomonas of each positive, negative and control group using nanobubbles in which air is enclosed, and a dark period of 12 hours per day is provided
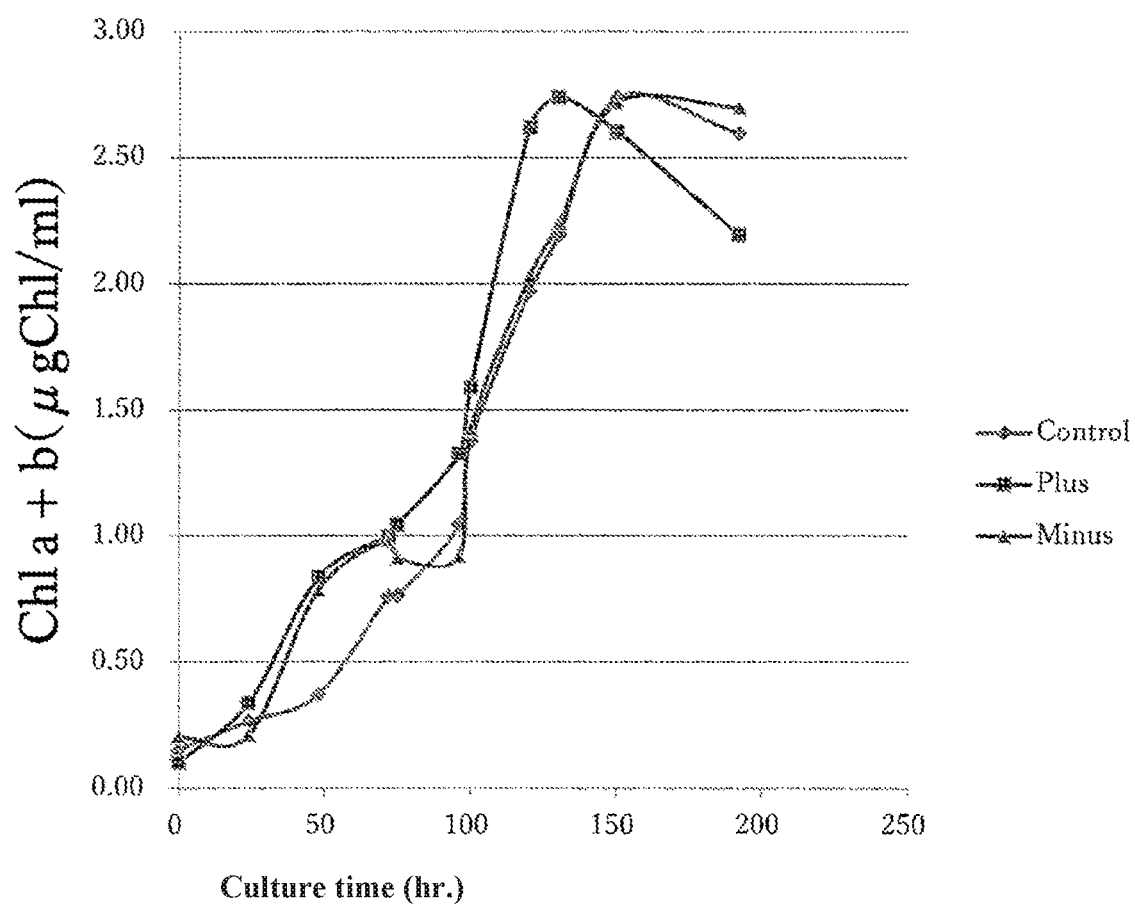

Fig. 6. Photographs of komatsuna on the 28th day after sowing, that show growth-promoting effects of positively and negatively charged nanobubbles in a Komatsuna LED-photosynthesis cultivation model
No Microbubbles
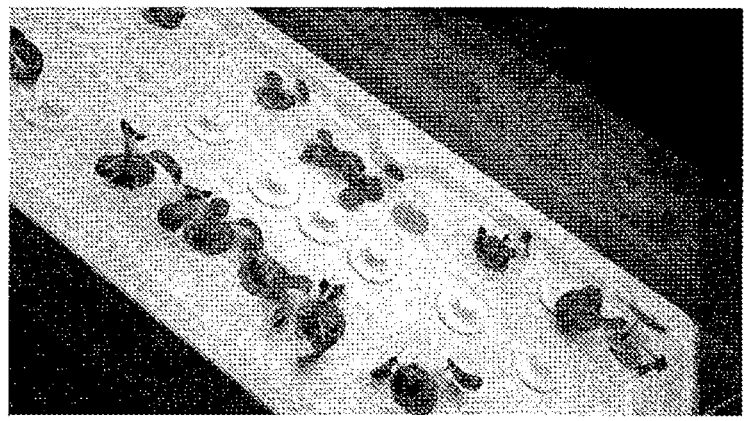
Positively (+) charged Nanobubbles
Negatively (−) charged Nanobubbles Microbubbles

Fig. 7. Effects of positively charged nanobubbles in a tomato greenhouse cultivation model
Cumulative yield amount of tomato from December 16, 2016 to June 16, 2017, in which a nanobubble generator that generates positively charged nanobubbles was introduced into the greenhouse in April 2017.
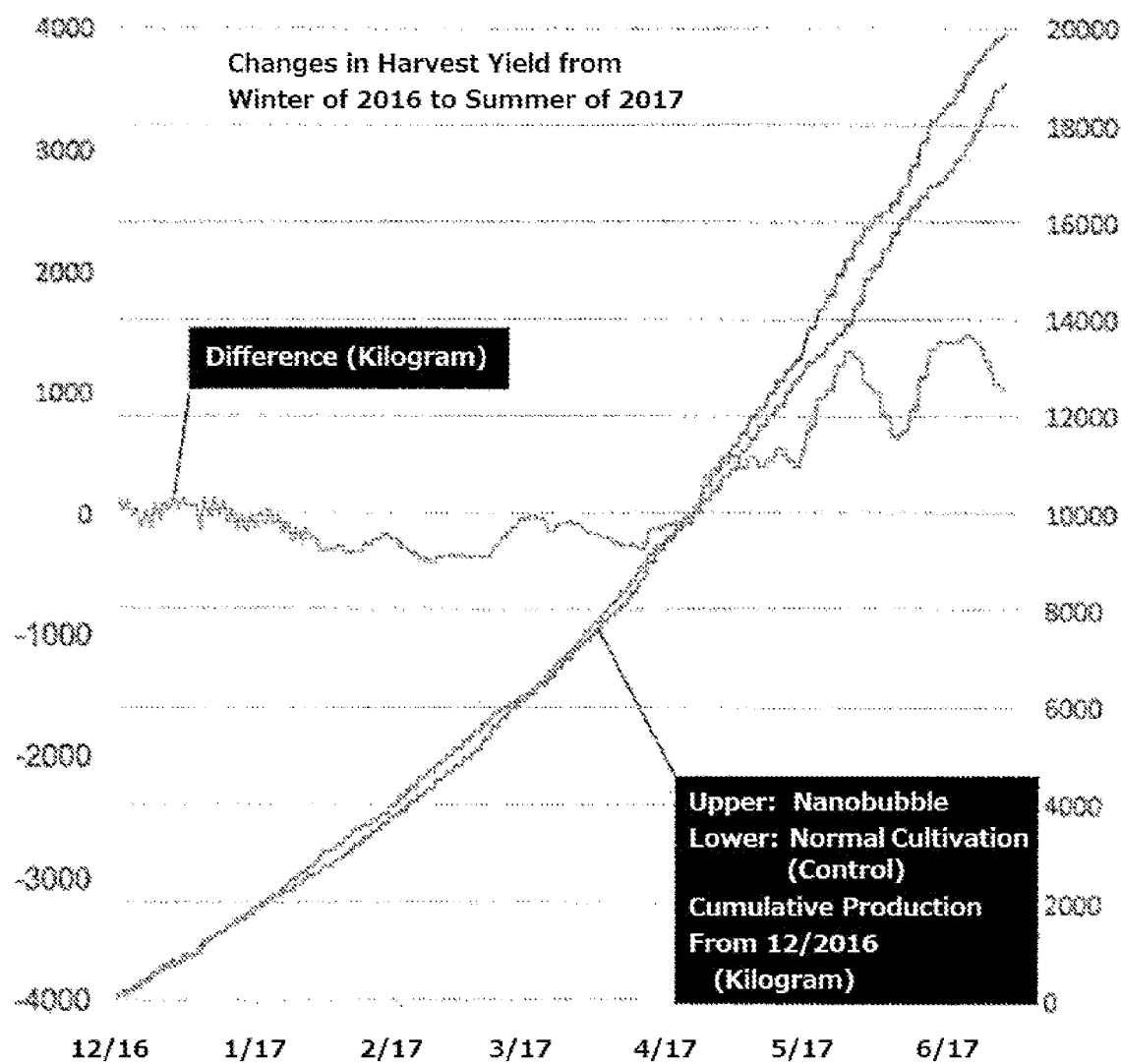

CHARGED NANOBUBBLE DISPERSION LIQUID, METHOD OF MANUFACTURING THE SAME, MANUFACTURING APPARATUS FOR THE SAME, AND A METHOD FOR CONTROLLING GROWTH RATE OF MICROORGANISMS AND PLANTS USING THE LIQUID

TECHNICAL FIELD

The present invention relates to a charged nanobubble dispersion liquid, a manufacturing method thereof and manufacturing apparatus therefor, and a method to control the growth rate of microorganisms and plants using nanobubble dispersion liquid. In particular, the present invention relates to a nanobubble dispersion liquid that has an electrostatic property, a manufacturing method to easily and inexpensively manufacture the nanobubble dispersion liquid, a manufacturing apparatus therefor, and a method to control the growth rate of microorganisms and plants using the nanobubble dispersion liquid.

BACKGROUND ART

A liquid containing bubbles less than 1 micrometer in diameter (so-called nanobubbles) has attracted attention for its properties that the bubbles stay in the liquid for a long time because the buoyancy of the bubbles is relatively small, and that the bubbles are negatively charged. Regarding suitable fields in which to apply such properties, liquid containing nanobubbles has been used, for example, to clean silicon wafers and increase aquaculture operations efficiency.

A method to generate nanobubbles in water has been proposed, as disclosed in Patent Document 1 (Japanese Patent No. 4144669).

A technology that uses nanobubbles to change the physiological activity of living things has also attracted attention. For example, Patent Document 2 (JP-A-2009-131769) discloses that nanobubbles can be used to promote plant growth.

PRIOR-ART DOCUMENT

Patent Document

Patent Document 1: Japanese Patent No. 4144669
Patent Document 2: JP-A-2009-131769

SUMMARY OF THE INVENTION

Problems to be Solved by the Invention

Conventional nanobubble technology has had the following problems: (1) nanobubble manufacturing costs have been high because conventional technology required a lot of energy to generate nanobubbles, which increased energy costs; (2) conventional nanobubble technology failed to generate positively charged nanobubbles; and in addition to economic problems, (3) areas to which the technology can be applied have been limited because it has been unclear what effects nanobubble have on living things.
(1) Nanobubble Manufacturing Costs
Previously proposed methods to generate nanobubbles include rotating a fan at high speed in a gas-liquid mixed phase flow, and applying high pressure to a flow to introduce that flow into a funnel-shaped tube to generate cavitation. Device structure tends to be complicated in such technologies, however, so price per device becomes expensive. Areas in which the technology can be applied have therefore been limited.

Also, because nanobubbles were generated in liquid phase, moving device parts received strong resistance from the liquid, which wasted a lot of energy. Consequently, areas to apply the technology have also been limited by economic inefficiency.
(2) Positive Charged Nanobubbles
Conventional technology was only able to generate negatively charged nanobubbles. Areas to apply the technology can be applied have been limited because such nanobubbles bind to positively charged ions or material surfaces.
(3) Nanobubble Effects on Living Things
Because conventional technology was only able to generate negatively charged nanobubbles, it was difficult to determine whether the effects of nanobubbles on living things were caused by (1) gas enclosed in the nanobubbles, (2) negative charge of the nanobubbles, or (3) physical collision with nanobubbles.

In order to address the aforementioned problems, the first objective of the present invention is to provide both positively and negatively charged nanobubbles.

The second objective of the present invention is to clarify the effects of positively and negatively charged nanobubbles on microbial and plant growth.

The other objective of the present invention is to provide a nanobubble manufacturing apparatus that is transportable, and that is capable of manufacturing nanobubbles where the nanobubbles are used, so that nanobubble technology can be implemented for agricultural facilities in rural areas and mountainous regions.

Means for Solving Problems

In order to address the mentioned problems, the present invention provides a charged nanobubble dispersion liquid that contains fine bubbles. The fine bubbles are dispersed in the liquid, are positively or negatively charged, have an average particle size of 10 nm to 500 nm, and have a zeta potential of 10 mV to 200 mV. The number of fine bubbles contained in the liquid is $10^5$ to $10^{10}$ per cc.

It is preferable that the charged nanobubble dispersion liquid is positively charged.

The present invention's manufacturing method for charged nanobubble dispersion liquid includes the steps of further crushing a liquid that has been crushed in a gaseous atmosphere to a micrometer size to generate nanobubbles that are enclosed by the liquid and that are charged, and collecting the generated nanobubbles using a force including gravity, centrifugal force, or electromagnetic force.

In the present invention, negatively charged nanobubbles are generated such that an electric field is applied to the gaseous atmosphere with grounding of the negative side, and positively charged nanobubbles are generated such that an electric field is applied to the gaseous atmosphere with grounding of a vibrating member that is used to crush the liquid.

A substance that binds or dissociates with cationic substances or anionic substances can be manufactured by using the method of manufacturing the charged nanobubble dispersion liquid of the present invention.

Also, an oxidizing agent or a reducing agent that depends on electrostatic properties of nanobubbles can be manufactured by using the method of manufacturing the charged nanobubble dispersion liquid of the present invention.

The growth of microorganisms can be promoted or suppressed, and the growth of plants can be promoted or suppressed by using the charged nanobubble dispersion liquid of the present invention.

Advantageous Effects of the Invention

Nanobubbles have been generated in a liquid phase, and the moving parts of nanobubble generating devices received strong resistance from the liquid, which wasted a lot of energy. Because of economic inefficiency, therefore, the areas to which the nanobubble technology can be applied have been limited.

In the present invention, however, the mechanism to generate nanobubbles is configured to be located in the gas phase, which has reduced energy consumption in manufacturing nanobubbles, and has significantly widened the areas to which the nanobubble technology can be applied.

Areas to which the subject technology can be applied are significantly widened because the nanobubble manufacturing apparatus of the present invention uses a simple structure to generate nanobubbles. Also, the apparatus has been reduced to a size transportable in small vehicles, which allows nanobubbles to be produced where they are used, and to implement the nanobubble technology for agricultural facilities in rural areas and mountainous regions.

The present invention achieved to separately manufacture positively and negatively charged nanobubbles by changing the combination of types of gas and liquid used when manufacturing nanobubbles. This allows supplying positively or negatively charged nanobubbles depending on the application.

Also, because the present invention enables separately manufacturing positively and negatively charged nanobubbles, the present invention makes it clear that nanobubbles have properties to give electrons to or accept electrons from substances.

Nanobubbles' properties to give electrons to or accept electrons from substances make it possible to manufacture, from only water and air, an oxidizing and a reducing agent, each of which has necessary oxidizing or reducing power, and is decomposed after a certain period of time. This nanobubble technology can be applied to removal of salt or radioactive substances from soil. This was difficult for conventional technology because it was impossible to implement this conventional technology due to concerns about serious secondary pollution, although using a large amount of an oxidizing or reducing agent can theoretically lead to eluviation of salt or radioactive substances from soil.

Furthermore, the present invention can generate positively charged nanobubbles, which makes it possible to conduct comparative experiments to clarify the effects of electrostatic properties of nanobubbles on living things. Experimental results show that using positively or negatively charged nanobubbles enables promoting or suppressing growth of microorganisms and plants. Promoting or suppressing growth of microorganisms or plants can be achieved such that nanobubbles of the present invention are introduced into, for example, tap water or culture solution, and the tap water or culture solution that contains nanobubbles is provided to microorganisms, or is absorbed through the roots or leaves of plants.

Microorganisms that are useful for society include those used for manufacturing pharmaceuticals, manufacturing biofuels, or brewing, and microorganisms that are harmful for society include pathogenic bacteria. The nanobubble technology of the present invention can timely suppress or promote the growth of these microorganisms.

BRIEF DESCRIPTION OF THE DRAWINGS

FIG. 1 shows a frequency distribution of positively charged nanobubbles by charge level measured using Zeta View.

FIG. 2 shows a frequency distribution of negatively charged nanobubbles by charge level measured using ZetaView.

FIG. 3 is a graph that shows chlorophyll production obtained by photosynthesis of chlamydomonas cultured in a medium containing nanobubbles in which air is enclosed.

FIG. 4 is a graph that shows chlorophyll production obtained by photosynthesis of chlamydomonas cultured in a medium containing nanobubbles in which carbon dioxide gas is enclosed.

FIG. 5 is a graph that shows chlorophyll production obtained by photosynthesis of chlamydomonas cultured in a medium containing nanobubbles in which air is enclosed, and that was provided with a dark period of 12 hours per day.

FIG. 6 contains photographs that show growth-promoting effects of positively and negatively charged nanobubbles in a Komatsuna LED-photosynthesis cultivation model.

FIG. 7 is a graph that shows the effects of positively charged nanobubbles in a tomato greenhouse cultivation model.

DESCRIPTION OF THE EMBODIMENTS

Hereinafter, embodiments and examples of the present invention will be described with reference to the accompanying drawings. This description is made to explain the present invention, and does not limit the technical scope of the present invention. It will be appreciated by those skilled in the art that changes and modifications may be made thereto without departing from the technical scope of the invention.

Preferably, positively or negatively charged nanobubbles of the present invention have an average particle size of 10 nm to 500 nm, and more preferably have an average particle size of 50 nm to 300 nm. If the average particle size of bubbles exceeds 500 nm, the buoyancy of the bubbles becomes large, which makes the bubbles to easily associate with each other, and causes the dispersion state of the bubbles to be unstable. Bubbles having an average particle size of less than 10 nm cannot be easily manufactured by the method of the present invention.

Preferably, positively or negatively charged nanobubbles of the present invention have a zeta potential of 10 mV to 200 mV, or −10 mV to −200 mV, and preferably have a zeta potential of 50 mV to 150 mV, or −50 mV to −150 mV. The nanobubbles having a zeta potential of 10 mV to −10 mV (excluding -10 mV) do not necessarily exhibit sufficient electrification effects, and it is difficult to charge nanobubbles below-200 mV or above 200 mV.

In addition, preferably the number of the charged bubbles contained in the nanobubble dispersion liquid of the present invention is $10^5$ to $10^{10}$ per cc, and more preferably $10^5$ to 109 per cc. If the number of charged bubbles contained in nanobubble dispersion liquid is less than $10^5$ per cc, nanobubbles may not exhibit sufficient effects of electrification, and it is difficult to manufacture a nanobubble dispersion liquid that contains nanobubbles exceeding 109 per cc.

In the charged nanobubbles of the present invention, positively charged nanobubbles are preferable than negatively charged nanobubbles. Although negatively charged nanobubbles have properties superior to those of non-charged nanobubbles, positively charged nanobubbles have properties generally superior to those of negatively charged nanobubbles.

(Manufacturing a Nanobubble Dispersion Liquid)

Nanobubbles used in the embodiments and examples are generated as follows. In a gaseous atmosphere, a liquid that has been crushed to a micrometer size is further crushed to generate nanobubbles that are enclosed by the liquid and that are charged. Generated nanobubbles are collected using a force including gravity, centrifugal force, or electromagnetic force to generate a charged-nanobubble dispersion liquid within the liquid.

Negatively charged nanobubbles are generated such that an electric field is applied to the gaseous atmosphere with grounding of the negative side, and positively charged nanobubbles are generated such that an electric field is applied to the gaseous atmosphere with grounding of a vibrating member that is used to crush the liquid.

FIG. 1 shows a frequency distribution of positively charged nanobubbles of Example 1 by the zeta potential measured using ZetaView, and FIG. 2 shows that of negatively charged nanobubbles of Example 2 by the zeta potential measured using ZetaView.

(Effects of Charged Nanobubbles)

The present invention provides a method of manufacturing charged nanobubbles, which react with substances so that the substances bind or dissociate with cationic or anionic substances.

Also, in the charged nanobubbles of the present invention, the nanobubbles have the properties to give to or accept electrons from substances, which makes it possible to manufacture, only from water and air, an oxidizing agent and a reducing agent that have necessary oxidizing or reducing power, and that are decomposed after a certain period of time.

Furthermore, the present invention can generate positively charged nanobubbles, which makes it possible to conduct comparative experiments to search the effects by electrostatic properties of nanobubbles on living things. Experimental results show that use of positively or negatively charged nanobubbles allows promoting or suppressing the growth of microorganisms and plants. Promoting or suppressing microorganism or plant growth can be made such that nanobubbles of the present invention are introduced into, for example, tap water or culture solution, so that the tap water or culture solution that contains nanobubbles is provided to microorganisms, or is absorbed through the roots or leaves of plants.

Example 1: Manufacturing Positively Charged Nanobubbles

Nanobubbles surrounded by water and positively charged were obtained by the following process: (1) water crushed to a micrometer size was supplied into a gaseous atmosphere in a closed state; (2) the water crushed to a micrometer size was further crushed using multiple rotating bodies arranged such that adjacent rotating bodies rotate in opposite directions; and (3) generated mist was collected. Density by diameter and density by charge of obtained nanobubbles were measured using nanobubble charge measurement equipment provided by MicrotracBEL, and calculated and determined by ZetaView+T. Ohdaira charge-disk method. The average bubble particle size was measured using the ultra-high voltage electron microscope of SPring 8 located in Hyogo Prefecture.

Density by charge of positively charged nanobubbles measured by ZetaView is shown in FIG. 1.

Example 2: Manufacturing Negatively Charged Nanobubbles

Nanobubbles surrounded by water and negatively charged were obtained by the following process: (1) water crushed to a micrometer size was supplied into a gaseous atmosphere in a closed state, in which an electric field was applied to the gaseous atmosphere, and the negative side was grounded; (2) the water crushed to a micrometer size was further crushed using multiple rotating bodies arranged such that adjacent rotating bodies rotate in opposite directions; and (3) generated mist was collected.

Density by charge of negatively charged nanobubbles is shown in FIG. 2.

(Method to Control of Microorganism and Plant Growth Rate Using Nanobubble Dispersion Liquid)

Example 3: Using Nanobubbles in which Air is Enclosed

The microorganism used was wild-type chlamydomonas (NIES-2235, *Chlamydomonas reinhardtii*, hereinafter "chlamydomonas"). *Chlamydomonas* was assigned to three groups; a group cultured by nutrient medium containing positively charged nanobubbles in which air is enclosed (positive group), a group cultured by a nutrient medium containing negatively charged nanobubbles in which air is enclosed (negative group), and a group cultured by a nutrient medium not containing nanobubbles (control group). Chlorophyll production of each group was measured.

Cultivated strain: chlamydomonas
NIES Strain No.: NIES-2235
Medium: C medium
Purchase source: National Institute for Environmental Studies, NIES collection

*Chlamydomonas* was placed in a flat petri dish, and continuously irradiated to *Chlamydomonas* from the upper side at a distance of 25 cm by light having peak wavelength of 620 nm to 630 nm, which is optimal for photosynthesis. HSM agar medium was used as medium.

Preparation of Test Medium Using Charged Nanobubbles
  Positive group: A medium was prepared using positively charged nanobubbles prepared by the method used in Example 1. Carbon dioxide was used as the gas to manufacture the positively charged nanobubbles.
  Negative group: A medium was prepared using negatively charged nanobubbles prepared by the method described in Example 2. Carbon dioxide was used as the gas to manufacture the negatively charged nanobubbles.
  Control group: A medium was prepared using distilled water containing no nanobubbles.

Chlorophyll was extracted from cultivated chlamydomonas at regular intervals using the chlorophyll extraction method with acetone. The obtained chlorophyll was measured by a spectrophotometer (NanoDrop ND-1000). The measurement results are shown in FIG. 3.

As shown in FIG. 3, the positive group showed a significant growth-rate increase of chlorophyll production, compared with the control group, in the induction phase and in the logarithmic growth phase. The growth rate of the negative group was lower than that of the control group.

Example 4: Using Nanobubbles in which Carbon Dioxide Gas is Enclosed

As in Example 3, each medium for the positive and negative groups were prepared using positively and negatively charged nanobubbles, which were manufactured in carbon dioxide gas. Chlorophyll production of each positive, negative, and control group was measured.
The measurement results are shown in FIG. 4

As in Example 1, the positive group grew faster than the control group, and the negative group grew slower than the control group.

Example 5: Using Nanobubbles in which Air is Enclosed, and a Dark Period of 12 Hours Per Day is Provided As in Example 3, each medium for the positive group and the negative group were prepared by using positively and negatively charged nanobubbles, and both of which were manufactured in carbon dioxide gas. The chlorophyll production of each of the positive group, negative group, and control group under the provision of a 12-hour dark period per day was measured.
The measurement results are shown in FIG. 5.

As shown in FIG. 5, the positive group grew faster than the control group, while the negative group grew in a rate similar to the control group.

Example 6: Komatsuna LED-Photosynthesis Cultivation Model

Water that contains positively charged nanobubbles or negatively charged nanobubbles was used for hydroponic culture of komatsuna, and the effects of each water on the growth of komatsuna were comparatively examined.
Cultivation Condition
  Temperature: 20° C. when LED was off, and 27° C. when LED was on
  Liquid fertilizer: Hyponext
  Nanobubble containing water: Prepared pursuant to Examples 1 and 2
  Average particle size of the bubbles: 180 nm (within the range of 100 nm to 200 nm)
  Bubble density: $3.0 \times 10^8$ bubbles per cc
  Nanobubble charge measurement: MicrotracBEL
  Method of calculation: ZetaView+T. Ohdaira charge-disk method
Photographs of komatsuna of the 28th day after sowing are shown in FIG. 6.

Example 7: Growth Difference in Radish Photosynthesis Model

Water that contains positively or negatively charged nanobubbles was used for hydroponic culture of radish to compare the effects of water containing charged nanobubbles.
The results are shown in Table 1

As shown in Table 1, water of the positively charged nanobubbles exhibits the growth rate of 1.7 to 2.2 times that of the control. Water of the negatively-charged nanobubbles exhibits the growth rate of 1.1 to 1.2 times that of the control.

TABLE 1

Growth difference in radish photosynthesis model

|  | Control | Positively charged nanobubbles | Negatively charged nanobubbles |
|---|---|---|---|
| Fibrous root length | 100 | 222 | 108 |
| Nutritive root volume | 100 | 171 | 119 |
| Leaf area | 100 | 165 | 117 |

Example 8: Yield Amount in Tomato Greenhouse Cultivation Model

Shown in FIG. 7 is a cumulative yield amount of tomato from Dec. 16, 2016 to Jun. 16, 2017, in which a nanobubble generator that generates positively charged nanobubbles was introduced into the greenhouse in April 2017.

As shown in FIG. 7, the yield of tomato grown in the greenhouse into which the positively-charged nanobubble generator was introduced increased significantly since April 2017. The yield of the tomato grown in the greenhouse into which the positively charged nanobubble generator was introduced increased by 11% from Apr. 16, 2017 to Jun. 16, 2017 compared with the yield of the tomato grown without a positively charged nanobubble generator.

The invention claimed is:
1. A method for promoting growth of plants, the method comprising:
  (a) applying a positively charged nanobubble dispersion liquid to the plants, wherein the positively charged nanobubble dispersion liquid is absorbed through the roots or leaves of the plants; and
  (b) the positively charged nanobubble dispersion absorbed in the plants increase chlorophyll production in the plants,
  wherein the positively charged nanobubble dispersion liquid has the following properties:
    (i) an average particle size of 10 nm to 500 nm;
    (ii) a zeta potential of +10 mV to +200 mV; and
    (iii) a dispersion density of $10^5$ to $10^{10}$ nanobubbles per 1 ml.

* * * * *